United States Patent [19]

Hilton et al.

[11] Patent Number: 4,871,668

[45] Date of Patent: Oct. 3, 1989

[54] MICROORGANISM ATCC53716 AND PROCESS FOR PRODUCING ACETOPHENONE

[75] Inventors: Matthew D. Hilton; Wendy J. Cain, both of Terre Haute, Ind.

[73] Assignee: Pitman-Moore, Inc., Terre Haute, Ind.

[21] Appl. No.: 220,085

[22] Filed: Jul. 18, 1988

[51] Int. Cl.$^4$ .......................... C12P 7/24; C12R 1/01; C12R 1/38
[52] U.S. Cl. .................................. 435/147; 435/822; 435/874
[58] Field of Search ................. 435/147, 874, 822

[56] References Cited

U.S. PATENT DOCUMENTS 4,751,077 6/1988 Bell et al. .......................... 424/85

OTHER PUBLICATIONS

Chemical Abstracts, Cox et al., Jul. 30, 1979; vol. 91(5); p. 287; H35386(m).

*Primary Examiner*—Ronald W. Griffin
*Assistant Examiner*—Pamela S. Webber
*Attorney, Agent, or Firm*—Wendell Ray Guffey; Thomas L. Farquer

[57] ABSTRACT

A microorganism of the genus Pseudomonas (ATCC 53716) metablizes cinnamate to produce acetophenone in a receoverable quantity upon fermentation in an aqueous nutrient medium containing cinnamate as a carbon source and, optionally, assimilable sources of nitrogen and inorganic substances.

5 Claims, No Drawings and particularly to a mutant microorganism of the genus Pseudomonas capable of metabolizing cinnamate to produce acetophenone.

BACKGROUND OF THE INVENTION

Acetophenone, 1-Phenylethanone, is commonly prepared from benzene and acetylchloride in the presence of aluminum chloride or catalytically from acetic and benzoic acids; Merck Index, 9th Edition. Acetophenone has many uses; e.g. in perfumery to impart an orange-blossom odor, as a catalyst for the polymerization of olefins, and in organic synthesis, particularly as a photosensitizer. Acetophenone is also used as a flavoring in foods. Acetophenone, however, has not been prepared using microorganisms or other biological techniques.

SUMMARY OF THE INVENTION

It is, therefore, an object of the present invention to provide a process for producing acetophenone.

It is another object of the present invention to provide a mutant microorganism capable of producing acetophenone.

It is another object of the present invention to provide a mutant microorganism capable of metabolizing cinnamate to produce acetophenone.

It is another object of the present invention to provide a culture of a mutant microorganism capable of metabolizing cinnamate to produce acetophenone.

These and other objects are achieved using a mutant microorganism of the genus Pseudomonas which metabolizes cinnamate to produce acetophenone. The parent strain of the mutant microorganism was isolated from soil samples taken in Terre Haute, IN and subjected to chemical mutagenesis to produce a novel mutant microorganism, now deposited with the American Type Culture Collection (ATCC) and designated ATCC 53716.

ATCC 53716 produces acetophenone when fermented using cinnamate as a carbon source. The acetophenone is separated from the fermentation medium and used as a flavoring in the food industry.

Other objects, advantages, and novel features of the present invention will become apparent from the following detailed description of the invention.

DETAILED DESCRIPTION OF THE INVENTION

The present invention comprises a mutant microorganism of the genus Pseudomonas that metabolizes cinnamate to produce acetophenone, a culture containing the microorganism, and a process for using the microorganism to produce acetophenone. An unrestricted deposit of this hitherto unknown mutant microorganism was made on Jan. 13, 1988 with the American Type Culture Collection Rockville, Maryland (ATCC) under the provisions of the Budapest Treaty and has been assigned the accession number ATCC 53716. Applicants have directed that the deposited strain be freely available to the general public upon issuance of a U.S. Patent citing the strain.

The mutant microorganism strain of the present invention was obtained by mutating a parent strain of bacteria which was isolated from a soil sample obtained in Terre Haute, IN. A small amount of the soil sample was inoculated into culture flasks containing nutrient media and the flasks were incubated at 30° C. with shaking. When the cultures grew to visible turbidity, a small amount of the culture was transferred to a second culture flask and grown until turbid. The turbid cultures were diluted and plated for colony isolation on agar containing sodium cinnamate. The parent strain for the present mutant microorganism was isolated because it grew well on nutrient media containing cinnamate as a major source of carbon. The parent strain was found to be a cinnamate-metabolizing, gram-negative, rod-shaped bacterium.

Cells of the parent strain were mutated with nitrosoguanidine and screened to identify mutants that exhibited poor growth on cinnamate. Several mutant isolates had a distinctive and pleasant aroma when streaked on cinnamate minimal media agar and when grown in shake flasks with cinnamate as a major source of carbon. A culture broth of the mutant microorganism of the present invention (ATCC 53716) had the most potent aroma and was therefore selected for further use and study.

The following is a summary of the taxonomic study and identifying characteristics of ATCC 53716:

Product Classification: The most important identifying characteristic of ATCC 53716 is its ability to metabolize cinnamate to produce acetophenone.

Cell Classification: ATCC 53716 has been classified as a member of the genus *Pseudomonas* which resembles *Pseudomonas acidovorans* and *Pseudomonas testosteroni*. These two strains comprise the acidovorans DNA homology group of the Pseudomonas rRNA group III. *Pseudomonas acidovorans* and *Pseudomonas testosteroni* are considered to be included in the species *Comamonas terrigene* by some taxonomists.

ATCC 53716 shares many common characteristics with the acidovorans group species *Pseudomonas acidovorans* and *Pseudomonas testosteroni;* e.g. lophotrichous flagellation, lack of gelatin and starch hydrolysis, accumulation of poly-beta-hydroxybutyrate, and inability to denitrify. Nutritionally these microorganisms are versatile; although they cannot metabolize glucose and most carbohydrates. These shared characteristics are shown in Table 1.

The characteristics that separate *Pseudomonas acidovorans* from *Pseudomonas testosteroni* are listed in Table 2. ATCC 53716 differs from the two described species in important ways and appears to fall somewhere in between these two group species.

Colonial Morphology: Although colony morphology depends somewhat on the age and handling of agar plates, in general the colonies appear thin, translucent and spreading on minimal medium (MM)+0.3 g/l Na benzoate+0.5 g/l yeast extract agar. Colonies on nutrient agar (Difco) begin round and "normal" looking (i.e. *Escherichia coli*-like), and later develop a halo of thin, translucent growth that seems to spread.

Cell Physiology and Biochemistry: ATCC 53716 is a gram-negative, motile, obligately aerobic, rod-shaped bacterium which grows at temperatures of 22° C. and 30° C., grows slowly at 16° C., and not at 37° C. or 42° C. on solid agar media with cinnamate and yeast extract as sources of carbon. The strain will grow at 30° C. on minimal media agar in which cinnamate is sole available source of carbon and grows faster on the same media with benzoate substituted for cinnamate. The cell physiology and biochemistry of ATCC 53716 is summarized in Table 3.

Nutritional Characteristics: ATCC 53716 accumulates poly-beta-hydroxybutyrate as a cellular reserve material, does not hydrolyse aesculin, casein, starch, or gelatin, and does not denitrify. Exogenous growth factors are not required for growth; ammonium salts can serve as sole nitrogen source. The strain grows on MacConkey's agar but not on 0.05% cetrimide. The strain is non-saccharolytic, producing an alkaline reaction aerobically in all oxidativ fermentative metabolism (OF) substrates except glycerol. Nutritionally it is quite versatile although it is unable to utilize carbohydrates and most sugar derivatives. The strain cannot utilize DL-arginine or betaine, but utilizes most fatty acids, dicarboxylic acids, hydroxy acids, and aliphatic amino acids. Data from growth on Hugh and Leifson's OF Medium and compounds useful as the sole carbon source in Stainer's Base are given in Tables 4 and 5, respectively.

Antibiotic Susceptibility: ATCC 53716 was tested for sensitivity to antibiotics. The results are shown in Table 6. Referring to Table 6, ATCC 53716 is highly resistant to most antibiotics tested.

According to the present invention, a process for producing acetophenone comprises aerobically fermenting a microorganism of the genus Pseudomonas having the identifying characteristics of ATCC 53716 in suitable aqueous nutrient media containing cinnamate as the source of carbon. Nitrogen, trace elements, inorganic salts and other factors required for efficient growth of the organism may also be included in the media. Preferably, the microorganism is in a biologically pure form.

Cinnamate can be used alone as the source of assimilable carbon in the nutrient media or in combination with other carbon sources such as glycerol, glutamate, lactate, benzoate, and the like. The exact quantity of the carbon source or sources utilized in the media depend in part upon the other ingredients in the media but the amount usually varies between about 0.5% and 5% by weight of the media.

Organic and inorganic nitrogen-containing materials can be used as nitrogen sources in the fermentation process. Suitable nitrogen sources include, for example, ammonium, yeast hydrolysates, primary yeast, soybean meal, cottonseed flour, hydrolysates of casein, corn-steep liquor, distiller's solubles or tomato paste and the like. The sources of nitrogen, either alone or in combination, are used in amounts preferably ranging from about 0.05% to 0.2% by weight of the aqueous media.

Inorganic salts can be incorporated in the culture media. Typical salts include salts capable of yielding sodium, potassium, ammonium, calcium, phosphate, sulfate, chloride, carbonate, and like ions. Also, trace metals such as cobalt, manganese, iron, magnesium, and the like can be included in the media.

Preferably, the media for culturing ATCC 53716 is a minimal media containing cinnamate as the carbon source, ammonium as the nitrogen source, and sufficient organic salts, trace elements, and other factors as required for efficient growth. The most preferred media is a minimal medium (MM) containing about 0.6 g/L $NaH_2PO_4$, 2.4 g/L $K_2HPO_4$, 1.0 g/L $(NH_4)_2SO_4$, and 0.5 g/L NaCl, 0.016 ml/L of a 1M $MgCl_2$, and 0.4 ml/L of an "iron mix" consisting of 0.1% $FeSO_4*7H_2O$ and 0.1% trisodium citrate, 0.5 g/L yeast extract (Difco) and 0.5 g/L sodium cinnamate (pH 7). For solid media, agar (Difco) is added to give 1.5% final concentration.

It should be emphasized that the media described herein are merely illustrative of the wide variety of media which may be employed by skilled artisans and are not intended to limiting the fermentation of the present microorganism to those media.

The fermentation is carried out at temperatures ranging from about 25°–35° C.; however, for optimum results it is preferable to conduct the fermentation at temperatures of about 30° C. The pH of the nutrient media for growing ATCC 53716 in culture and producing acetophenone can vary from about 6 to about 8, preferably about 7.

A small scale fermentation is conveniently carried out by inoculating a suitable nutrient medium with the microorganism or culture and, after transfer to a production medium, permitting the fermentation to proceed at a constant temperature of about 30° C. on a shaker for about 1–3 days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1–2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the content of the flasks are recovered by extraction with a suitable solvent such as methylene chloride.

Large scale fermentations are preferably conducted in suitable tanks provided with an agitator and a means of aerating the fermentation medium. Accordingly, the nutrient medium is made up in the tank and sterilized by heating at temperatures of up to about 121° C. Upon cooling, the sterilized medium is inoculated with a previously grown seed of the producing microorganism or culture. The fermentation is permitted to proceed for a period of time as, for example, from 3–6 days while agitating and/or aerating the nutrient medium and maintaining the temperature at about 30° C.

On completion of the fermentation, acetophenone can be recovered by any suitable means; preferably by treatment of the fermentation beer with an immiscible solvent which extracts the acetophenone but does not extract the other medium components. The quantity of solvent employed generally ranges from about 2 to about 3 volumes per volume of fermentation beer. Among the various solvents which may be employed are ethyl acetate, petroleum ether and some halogenated hydrocarbons such as methylene chloride, carbon tetrachloride, chloroform, and trichlorofluoromethane, preferably methylene chloride.

Alternatively, acetophenone can be recovered from the exit gas of air-sparged fermentations by any suitable means such as condensation or filtration of exit gas through activated charcoal, followed by stripping of the charcoal with a suitable solvent such as methylene chloride.

The acetophenone may be used for many suitable purposes, e.g. perfume, catalyst, and the like, but is commonly used in the flavoring industry as a component of honey, strawberry and plum flavors.

According to the present invention, a culture of the microorganism of the genus Pseudomonas having the identifying characteristics of ATCC 53716 capable of metabolizing cinnamate to produce acetophenone in a recoverable quantity upon fermentation in an aqueous nutrient medium containing cinnamate as the carbon source is provided. The culture can be prepared in any convenient form but is preferably in a freeze dried form containing the microorganism, preferably in a biologically pure form.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Mutagenesis and Screening Procedure: The parent strain for ATCC 53716 was isolated from a soil sample in Terre Haute, IN. It was found to be a cinnamate-metabolizing, Gram-negative, rod-shaped bacterium.

Mutagenesis: Log phase cells of the parent strain soil isolate were mutagenized by treatment with N-methyl-N'-nitro-N-nitrosoguanidine by an adaptation of standard methods as disclosed in Miller, *Experiments in Molecular Genetics-Nitrosoguanidine Mutagenesis*, pages 125-129 (1972). Treatment was with 5 µg/ml mutagen for 30 minutes at 30° C., after which cells were sedimented and washed to remove residual mutagen. Mutated, washed cells were frozen at −70° C. and stored for further use and study.

Screening: Mutated cells were screened for acquisition of a defect in cinnamate metabolism by plating on agar plates containing MM +0.5 g/l sodium benzoate (pH 7) and replica plating to the same medium and the same with cinnamate substituted for benzoate. Colonies which grew poorly on cinnamate but normally on benzoate (compared to the parent strain) were picked for further analyses. In some cases the mutagenized cells were enriched for prototrophy and a functional benzoate-downstream pathway by growth on benzoate-MM broth prior to plating. In those cases only one or a few colonies were picked from the plate screen based on the assumption that duplicates from one enrichment would be siblings.

Several mutant isolates had a distinctive and pleasant aroma when streaked on cinnamate minimal medium agar and when grown in shake flasks with cinnamate as a major source of carbon. Culture broths of mutants had the most potent aromas and were selected for further study. Selected isolates, including ATCC 53716, were routinely grown on benzoate MM broth and frozen at −70° C. for archival purposes.

In an effort to identify the unknown compound, several of the isolates, including ATCC 53716, were subsequently inoculated into 100 ml volumes of MM +0.5 g/l yeast extract +0.5 g/l cinnamate medium in shake flasks (500 ml Erlenmeyers) and incubated at 30° C. until turbid. Extraction of the unknown compound from the broth was routinely done by passing a 25 or 50 ml volume of culture supernatant over a 100 mg C-18 silica pre-packed column (Analytichem International) and eluting with 1/100th volume of methanol. Broths or their extracts were routinely assayed by HPLC or a colorimetric assay for total aldehydes and ketones as described in Examples 2 and 3 below.

EXAMPLE 2

Detection and Identification of the Unknown Compound by Reverse Phase HPLC: Extracts of fermentation broths in which cinnamate was the primary source of carbon were analyzed by reversed phase HPLC using the following procedure: Samples of 20 µl or 10 µl were manually injected onto a 250×4.6 mm, 5 micron C-18 column from ISCO. The eluant was formed with two pumps under the control of the ISCO Chem-Research program run on an IBM personal computer. Flow rate was 1 ml/min beginning with an initial mix of 50% B (eluant B, methanol; eluant A, milliQ water (Millipore Corp.); each containing 0.1% (v/v) glacial acetic acid), increasing at a constant rate to 55% B over 12 minutes, then returning to 50% B during the final 2 minutes. Analytes were detected with an in-line UV-visible detector (ISCO V-4) set for 250 nm wavelength and 0.05 AUFS sensitivity. When necessary, peaks were collected from the effluent in 0.5 ml samples with a fraction collector (ISCO model Foxy).

Initially the objective was simply to determine if benzaldehyde was present. Little was seen. However, a peak which eluted between benzaldehyde and cinnamic acid was evident in the extracts of the strain later designated ATCC 53716. A smaller amount of this compound was also evident in extracts of the broth of the unmutated parent strain. This peak was observed regardless of whether the pH of the broth was lowered prior to extraction, indicating that the analyte detected was not an acid. The compound was subsequently proven to be acetophenone (Example 5).

EXAMPLE 3

Detection and Identification of the Unknown Compound by Reaction With 2,4-Dinitrophenylhydrazine: It was noted that some component of the crude broth reacted with 2,4-dinitrophenylhydrazine (DNPH), indicating the presence of the carbonyl oxygen of an aldehyde or ketone. To determine if the analyte responsible for the 9 minute HPLC peak was an aldehyde or ketone, fractions were collected from the effluent stream from the UV absorbance detector of the HPLC and assayed for reaction with DNPH as described in Harayama et al., *J. Bacteriol.*, 167:455-461 (1986). The sum of the sample plus water was adjusted to 1.5 ml, then 0.15 ml of 0.5 mg/ml 2,4-dinitrophenylhydrazine in 2 N HCl was added and vortexed briefly prior to incubation at 30° C. for 15 minutes. 0.6 ml of 5 N NaOH followed by 1.2 ml of ethanol (both preheated to 60° C.) were added in rapid succession and samples were vortexed to homogeneity. Absorbance was read at 440 nm. The reactive material elutes with the same retention time as the unknown compound indicating that the unknown contains an aldehyde or ketone functional group. The compound was subsequently proven to be acetophenone (Example 5).

EXAMPLE 4

Radiotracer Demonstrates Unknown is Derived From Cinnamate: Whereas it was highly probable that the unknown compound detected was derived from the cinnamate based on its UV absorbance, we used 7-labeled [$^{14}$C-]cinnamate as a radiotracer to confirm this. A culture of the strain later designated ATCC 53716 was prepared by incubation overnight on minimal media-yeast extract (MM-YE) medium containing 0.5 g/l cinnamate. When most of the cinnamate was utilized, as shown by the absorbance at 266 nm, 5 uCi of 14C-cinnamic acid were added to the culture. After 2 hours the cells were removed and the supernatant extracted and analyzed by HPLC. Again, as seen with the DNPH carbonyl assay, the major radioactive peak coincides perfectly with the major UV absorbing peak around 8.7 minutes retention time indicating that the unknown is derived from cinnamate.

EXAMPLE 5

Positive identification of unknown as acetophenone using GC/MS: A 50 ml broth supernatant from the fermentation of ATCC 53716 was analyzed with a gas chromatograph connected to a mass spectrometer. The retention time and mass spectrum established the identity of the unknown analyte as being acetophenone. Essentially only acetophenone was evident; a concentration of 300 ppm or 0.3 g/l of acetophenone was indicated. Gas chromatography analysis out to 75 minutes revealed no additional peaks greater than 1 ppm.

Collectively, Examples 2-5 show that the mutant microorganism later designated ATCC 53716 is metabolizing cinnamate to produce acetophenone.

EXAMPLE 6

Utilization of Acetophenone by the Parent Strain: The parent strain was inoculated into standard broths containing minimal salts plus 0.5 g/l yeast extract (to assure growth), one of which had been supplemented with 0.25 g/l acetophenone. Diluted samples of the culture, taken immediately after inoculation and after incubation for 3 to 4 days, were analyzed for the concentration of acetophenone present. They were equivalent (0.25 g/1), while a control flask, in which 0.5 g/l cinnamate was included in place of the acetophenone, had no residual cinnamate. This shows that the parent strain does not utilize acetophenone. Similarly, ATCC 53716 would not be expected to utilize acetophenone.

EXAMPLE 7

Inhibition of Growth of the parent strain by Acetophenone: Because of the hydrophobic nature of acetophenone it is expected to be toxic to microbial cells, including those that produce it. A turbid culture of the parent strain was used to inoculate a series of flasks, each containing minimal salts plus 0.5 g/l yeast extract and increasing quantities of acetophenone. The cultures were incubated with shaking for 20 hours at 30° C. and final turbidities were determined. Essentially all growth was inhibited by the presence of 2 g/l acetophenone and growth was inhibited 50% at a concentration of 1 g/l. Similar inhibition can be expected for ATCC 53716.

EXAMPLE 8

Spontaneous Conversion of a Compound Present in Fermentation Broth to Acetophenone: In an attempt to reconcile the higher titers determined by the DNPH colorimetric assay than determined by HPLC, a standard broth of ATCC 53716 was diluted in methanol and injected for HPLC analysis 5 times over a 2 to 3 hour time period with the intent of getting a statistically significant value for the titer. To our surprise, the acetophenone peak appeared to get progressively larger, while the other significant peak (near 5 min. retention time) became smaller. These results are shown in Table 7. An acetophenone standard was run 3 times on the same day and was reproducible to within 2%, thus it is unlikely that peak variability in the fermentation sample was the result of injection variability. In addition, the sum of the areas under the 5 minute peak and the acetophenone peak is essentially constant indicating a constant amount of UV absorbing material and spontaneous conversion of the 5 minute compound to acetophenone.

EXAMPLE 9

Media and Culture Conditions: Fermentation of ATC 53716 was routinely performed at 30° C. on a minimal medium (MM) containing, in g/l: $NaH_2PO_4$, 0.6; $K_2HPO_4$, 2.4; $(NH_4)_2SO_4$, 1.0; NaCl, 0.5. After autoclaving, two filter sterilized solutions were added aseptically (per liter) 0.016 ml 1M $MgCl_2$; 0.4 ml "iron mix" (0.1% $FeSO_4*7$ $H_2O$, 0.1% trisodium citrate). Except where otherwise stated, 0.5 g/l yeast extract (Difco) and 0.5 g/l sodium cinnamate (pH 7) was added to form a complete growth medium. For solid media, agar (Difco) was autoclaved separately and combined to give 1.5% final concentration.

Profiles of Simple Fermentations: A shake flask, initially containing 100 ml MM+0.5 g/l yeast extract+0.5 g/l cinnamate, was inoculated with ATCC 53716 and incubated at 30° C. for several days. At several time points during incubation samples were withdrawn. A portion of the samples were frozen for later determination of acetophenone concentration and a portion was used for immediate determination of culture turbidity (A-600 nm) and cinnamate concentration (inferred from A-266 nm, 1 A-266 U=ca. 7 mg/l cinnamate). At several times additional cinnamate was added. Approximate levels of productivity of acetophenone were determined from the data and are summarized in Table 8.

EXAMPLE 10

Two Stage Fermentation: Because of the relatively high cost of natural cinnamate and the cost and complexity of yeast extract, the possibility of a two stage fermentation was tested. ATCC 53716 and the parent strain were inoculated into MM+2.5 g/l glutamate, Na (pH 6.8), and shaken at 30° C. overnight to develop cell mass. This constituted the first stage of fermentation. Cinnamate was added two times and the concentrations of cells, residual cinnamate and accumulated acetophenone were monitored for the next day. Acetophenone was produced using this procedure, demonstrating the utility of a 2-stage fermentation.

Obviously many modifications and variations of the present invention are possible in light of the above teachings. It is therefore to be understood that within the scope of the appended claims the invention may be practiced otherwise than as specifically described.

TABLE 1

| Characteristics of Acidovorans Group | | |
|---|---|---|
| | Acidovorans* Group | ATCC 53716 |
| PHB Accumulation | + | + |
| Lophotrichous | + | + |
| Aerobic | + | + |
| Growth at 4 or 41 | − | − |
| Gelatin Hydrolysis | − | − |
| Lecithinase | − | − |
| Oxidase | + | + |
| Starch Hydrolysis | − | − |
| Tween 80 | + | + |
| Denitrification | − | |
| Utilization as Sole Carbon source: | | |
| L-Arabinose | − | − |
| D-Glucose | − | − |
| 2-Ketogluconate | − | − |
| Pelargonate | − | − |

TABLE 1-continued
Characteristics of Acidovorans Group

| | Acidovorans* Group | ATCC 53716 |
|---|---|---|
| Adipate | + | + |
| Sebacate | + | + |
| M-Hydroxybenzoate | + | + |
| Norleucine | + | + |
| Putrescine | − | − |

*Data from Bergey's Manual of Systematic Bacteriology, Vol. 1, Williams and Wilkins, (1984) and Stanier et al., The Aerobic Pseudomonads: A Taxonomic Study, J. Gen. Microbiol. 43, 159-271 (1966).

TABLE 2
Differences Between Pseudomonas Acidovorans And Pseudomonas Testosteroni

| | Pseudomonas acidovorans | Pseudomonas testosteroni | ATCC 53716 |
|---|---|---|---|
| Utilization as Sole Carbon Source: | | | |
| Fructose | + | − | − |
| D-Mannitol | + | − | − |
| L-Tartrate | + | − | − |
| Quinate | + | − | + |
| Ethanol | + | − | + |
| D-Tryptophan | + | − | − |
| L-Tryptophan | + | − | + |
| Benzoate | − | d | − |
| B-Alanine | + | − | − |
| Acetamide | + | − | − |
| Testosterone | − | + | − | d = 11-89% of strains are positive.

TABLE 3
Physiology & Biochemistry

| | ATCC 53716 | Pseudomonas testosteroni* | Pseudomonas acidovorans* |
|---|---|---|---|
| Gram positive | − | − | − |
| Gram negative | + | + | + |
| Gram variable | − | − | − |
| Motile at 37° C. | + | + | + |
| Motile at RT | + | + | + |
| Flagella peritrichous | − | − | − |
| Flagella lophotrichous | + | + | + |
| Flagella monotrichous | − | − | − |
| Flagella lateral | − | − | − |
| 4° C. growth | − | − | − |
| 25° C. growth | + | + | + |
| 30° C. growth | + | + | + |
| 37° C. growth | + | + | + |
| 41° C. growth | − | − | − |
| Fluorescein produced | − | − | − |
| Pycyanine produced | − | − | − |
| Diffusible orange | − | − | − |
| Diffusible yellow | − | − | − |
| Diffusible purple | − | − | − |
| Non-diffusible green | − | − | − |
| Other non-diff. pigments | − | − | − |
| Melanin pigment produced | − | − | − |
| pH 6.0 growth | + | nd | nd |
| 3% NaCl growth | + | + | + |
| 6.5% NaCl growth | − | − | − |
| MacConkey agar growth | + | d | + |
| Skim milk agar growth | + | nd | nd |
| Aesculin hydrolysis | − | − | − |
| Casein hydrolysis | − | nd | nd |
| Starch hydrolysis | − | − | − |
| Gelatinase | − | − | − |
| Tween 20 hydrolysis | + | nd | nd |
| Tween 80 hydrolysis | + | + | + |
| Indole | − | − | − |
| Simmons citrate growth | + | + | + |
| Urease | − | − | − |
| Nitrate to nitrite | + | + | + |
| Nitrite reduction | − | nd | nd |
| Nitrite to nitrogen gas | − | − | − |
| Hydrogen sulfide (TSI) | − | − | − |
| Lysine decarboxylase | − | − | − |
| Arginine (Mollers) | − | − | − |
| Ornithine decarboxylase | − | − | − |
| Phenylalanine deamination | − | − | − |
| Lecithinase | − | − | − |
| Phosphatase | w | nd | nd |
| Catalase | + | nd | nd |
| Oxidase | + | + | + |
| Gluconate oxidation | − | nd | nd |
| Growth on malonate as SCS | + | − | + |
| Tyrosine degradation | + | nd | nd |
| dl-hydroxybutyrate growth | + | + | + |
| PHB accumulation | + | + | + |
| Growth on 0.05% cetrimide | − | − | d |
| Growth on acetate as SCS | + | + | + |
| Testosterone deg. | − | + | − |
| 3-ketolactose from lactose | − | nd | nd | nd = no data
w = weakly positive
d = 11-89% of strains positive.
*Data from Bergey's Manual and Clark et al., Identification of Unusual Pathogenic Gram-Negative Aerobic and Facultatively Anaerobic Bacteria, U.S. Dept. of Health and Human Services, the Center for Disease Control (CDC), Atlanta, GA (1984)

TABLE 4
Growth on Hugh and Leifson's OF Medium**

| | ATCC 53716 | Pseudomonas testosteroni | Pseudomonas acidovorans |
|---|---|---|---|
| Acid from: | | | |
| L-Arabinose | K | | |
| Cellobiose | K | | |
| Ethanol | K | | |
| D-Fructose | K | K | + |
| D-Glucose AO2 | − | K | K |
| D-Glucose AnO2 | + | | |
| Alkaline pH in D-glucose | + | | |
| Acid from: | | | |
| Glycerol | + | | |
| i-Inositol | K | | |
| Lactose | K | K | K |
| Maltose | K | K | K |
| D-Mannitol | K | K | K |
| D-Mannose | K | K | K |
| L-Rhamnose | K | K | K |
| D-Ribose | K | | |
| Sucrose | K | K | K |
| Trehalose | K | | |
| D-Xylose | K | K | K |
| Control | K | | |

K = alkaline
*Data from Clark et al. and Hugh and Gilardi, Pseudomonas. In. E.H. Lennette, Manual of Clinical Microbiology, 3rd Edition, ASM, Washington, DC (1980).
**Hugh and Leifson, J. Bacteriol., 66, 24-26 (1953)

TABLE 5
Sole Carbon Sources in Stanier's Base

| | ATCC 53716 | Pseudomonas testosteroni* | Pseudomonas acidovorans* |
|---|---|---|---|
| L-Arabinose as SCS | − | − | − |
| Cellobiose as SCS | − | − | − |
| D-Fructose as SCS | − | − | + |
| D-Glucose as SCS | − | − | − |
| Lactose as SCS | − | − | − |
| Maltose as SCS | − | − | − |
| D-Mannitol as SCS | − | − | + |
| L-Rhamnose as SCS | − | − | − |
| D-Ribose as SCS | − | − | − |
| D-Sorbitol as SCS | − | − | − |
| Sucrose as SCS | − | − | − |
| Trehalose as SCS | − | − | − |

TABLE 5-continued

| Sole Carbon Sources in Stanier's Base | | | |
|---|---|---|---|
| | ATCC 53716 | Pseudomonas testosteroni* | Pseudomonas acidovorans* |
| D-Xylose as SCS | − | − | − |
| Adonitol as SCS | − | − | − |
| Erythritol as SCS | − | − | − |
| Glycerol as SCS | + | − | d |
| Ethanol as SCS | − | − | + |
| i-Inositol as SCS | − | nd | nd |
| Sebacic acid as SCS | + | + | nd |
| Acetamide as SCS | − | − | + |
| Adipate as SCS | + | + | + |
| Benzoate as SCS | − | d | − |
| Butyrate as SCS | + | + | + |
| Citraconate as SCS | + | + | + |
| D-Gluconate as SCS | + | + | + |
| M-Hydroxybenzoate as SCS | + | + | + |
| 2-Ketogluconate as SCS | − | − | − |
| DL-Lactate as SCS | + | + | + |
| L-Malate as SCS | + | + | + |
| Pelargonate as SCS | − | − | − |
| Propionate as SCS | + | + | + |
| Quinate as SCS | + | − | + |
| Succinate as SCS | + | + | + |
| L-Tartrate as SCS | − | − | + |
| Valerate as SCS | + | + | + |
| B-Alanine as SCS | − | − | d |
| D-A-Alanine as SCS | + | + | + |
| Betaine as SCS | − | − | − |
| Glycine as SCS | + | + | + |
| L-Histidine as SCS | + | + | + |
| DL-Norleucine as SCS | + | + | + |
| L-Proline as SCS | + | + | + |
| D-Tryptophan as SCS | − | − | + |
| L-Valine as SCS | − | d | − |
| DL-Arginine as SCS | − | − | − |
| Benzylamine as SCS | − | − | − |
| Futylamine as SCS | − | − | − |
| Putrescine as SCS | − | − | − |
| Mesaconate as SCS | + | d | + |
| DL-Glycerate as SCS | + | + | + |
| L-Tryptophan as SCS | + | − | + |
| Methanol as SCS | − | nd | nd | nd = no data
d = 11–89% of strains are positive.
*Data from Bergey's Manual

TABLE 6

| Antibiotic Susceptibility Tests | |
|---|---|
| Antibiotic | Minimal Inhibitory Concentration (μg/ml) |
| Ampicillin | > 400 |
| Carbenicillin | > 400 |
| Erythromycin | 200 |
| Kanamycin | 50 |
| Lincomycin | > 400 |
| Nalidixic Acid | 6 |
| Neomycin | > 400 |
| Rifampicin | 200 |
| Spectinomycin | 100 |
| Streptomycin | > 400 |
| Tobramycin | 100 |
| Trimethoprim | > 400 |

TABLE 7

Evidence for Conversion of the Unknown Compound With a Retention Time of 5 Minutes to Acetophenone

| | | Areas Under Peaks* (arbitrary units) | | |
|---|---|---|---|---|
| Run | Time | 5 min. | Acetophenone | Sum |
| 1 | 12:05 | 63748 | 34203 | 97,951 |
| 2 | 12:35 | 55871 | 46080 | 101,951 |
| 3 | 13:07 | 48114 | 56307 | 104,421 |
| 4 | 13:24 | 45015 | 60494 | 105,509 |
| 5 | 13:57 | 34451 | 68036 | 102,487 |

*An experimental error of <2% is estimated based on 10 μg/ml acetophenone standard run in triplicate: 30969, 30402, 29888; average 30420; standard deviation (n-1) = 540.

TABLE 8

Summary of Acetophenone Shake Flask Fermentation*

| Productivity | Units | ATCC 53716 |
|---|---|---|
| VS Time | g AcPh**/l/hr | 0.01 |
| Conversion | g AcPh/g Cinnamate | 0.15 |
| Per cell density | g AcPh/A-600 | nd*** |

*Bioconversion of cinnamate to acetophenone ATCC 53716. Titers reported are derived from 2,4-dinitrophenylhydrazine assay of crude broths from the 47 to 63 hour stage of the fermentations.
**AcPh=acetophenone.
***nd, not determined because cell density was increasing rapidly throughout the time period.

What is claimed is:

1. The microorganism ATCC 53716.
2. A process for producing acetophenone, comprising:
   fermenting the mircoorganism ATCC 53716 in an aqueous nutrient medium containing cinnamate as the carbon source; and
   recovering the acetophenone formed during the fermentation.
3. The process of claim 2 wherein assimilable sources of nitrogen, trace elements, and inorganic salts are added to the medium.
4. A culture of the microorganism ATCC 53716, said culture being capable of metabolizing cinnamate to produce acetophenone in a recoverable quantity upon fermentation in an aqueous nutrient medium containing cinnamate as the carbon source.
5. The culture of claim 4 in a freeze dried form.

* * * * *

UNITED STATES PATENT AND TRADEMARK OFFICE
CERTIFICATE OF CORRECTION

PATENT NO. : 4,871,668
DATED : October 3, 1989
INVENTOR(S) : Matthew D. Hilton & Wendy J. Cain It is certified that error appears in the above-identified patent and that said Letters Patent is hereby corrected as shown below:

Column 3, line 11, "oxidativ" should read --oxidative--

Column 8, line 8, "ATC" should read --ATCC--

Column 12, line 33, Claim 2, "mircoorganism" should read
          --microorganism--

In the Abstract, line 2, "metablizes" should read --metabolizes--

In the Abstract, line 3, "receoverable" should read
          --recoverable--

Signed and Sealed this

Sixth Day of November, 1990

Attest:

HARRY F. MANBECK, JR.

*Attesting Officer*    *Commissioner of Patents and Trademarks*